United States Patent
Welt et al.

(10) Patent No.: US 6,652,853 B2
(45) Date of Patent: Nov. 25, 2003

(54) METHOD FOR TREATING CANCER USING A33 SPECIFIC ANTIBODIES AND CHEMOTHERAPEUTIC AGENTS

(75) Inventors: Sydney Welt, New York, NY (US); Nancy Kemeny, New York, NY (US); Gerd Ritter, New York, NY (US); Achim A. Jungbluth, New York, NY (US); Leonard Cohen, New York, NY (US); Lloyd J. Old, New York, NY (US)

(73) Assignees: Ludwig Institute for Cancer Research, New York, NY (US); Sloan Kettering Institute for Cancer Research, New York, NY (US)

( * ) Notice: Subject to any disclaimer, the term of this patent is extended or adjusted under 35 U.S.C. 154(b) by 148 days.

(21) Appl. No.: 09/800,522

(22) Filed: Mar. 8, 2001

(65) Prior Publication Data

US 2002/0187144 A1 Dec. 12, 2002

(51) Int. Cl.$^7$ ...................... A61K 39/395; A61K 39/40; A61K 39/42
(52) U.S. Cl. ................................ 424/133.1; 424/135.1; 424/136.1; 424/138.1; 424/141.1; 424/152.1; 424/155.1; 424/156.1; 424/172.1; 424/174.1
(58) Field of Search .......................... 424/178.1, 181.1, 424/133.1, 135.1, 136.1, 138.1, 141.1, 152.1, 155.1, 156.1, 172.1, 174.1

(56) References Cited

U.S. PATENT DOCUMENTS 6,346,249 B1 * 2/2002 Barbas et al.

FOREIGN PATENT DOCUMENTS

WO 98/22149 * 5/1998

OTHER PUBLICATIONS

Welt et al (J. of Clin. Oncology vol. 12, No. 8 pp. 1561–1571), Aug. 1994.*
Lay (*Current Surgical Diagnosis & Treatment* 9$^{th}$ pp. ED 1224–1228), 1991.*
John E. Byfield et al., Pharmacologic Requirements for Obtaining Sensitization of Human Tumor Cells In Vitro to Combined 5–Fluorouracil or Ftorafur and X Rays, Int. J. Radiation Oncology Biol. Phys. Vo. 8, pp. 1923–1933 (1982).

Sheryl L. Parker et al., Cancer Statistics, CA Cancer J. Clin. vol. 47 No. 1 pp. 5–27, (1997).
James E. Krook, M.D., et al., Effective Surgical Adjuvant Therapy for High–Risk Rectal Carcinoma, The New England Journal of Medicine, vol. 324, No. 11 pp. 709–715 (1991).
John A. Laurie et al., Surgical Adjuvant Therapy of Large–Bowel Carcinoma: An Evaluation of Levamisole and The Combination of Levamisole and Fluorouracil, Journal of Clinical Oncology, vol. 7, No. 10 pp. 1447–1456 (1989).
Henry T. Lynch et al., Hereditary Colorectal Cancer, Seminars in Oncology, vol. 18, No. 4, pp. 337–366 (1991).
Mohammed Mohiuddin et al., Adjuvant Radiation Therapy for Colon and Rectal Cancer, Seminars in Oncology, vol. 18, No. 5 pp. 441–420 (1991).
Nicholas Petrelli et al., The Modulation of Fluorouracil With Leucovorin in Metastatic Colorectal Carcinoma: A Prospective Randomized Phase III Trial, Journal of Clinical Oncology, vol. 7, No. 10 pp. 1419–1426 (1989).
Martin Segerling et al., Enhancing Effect by Metabolic Inhibitors on the Killing of Tumor Cells by Antibody and Complement, Cancer Research, vol. 35, pp. 3195–3203 (1975).
Segerling et al., Chemotherapeutic Drugs Increase Killing of Tumor Cells by Antibody and Complement, Science, Bol. 188, pp. 55–57 (1975).
P.S. Weinstein, et al. Acute–Phase Proteins or Tumour Markers: The Role of SAA, SAP, CRP and CEA as Indicators of Metastasis in a Broad Spectrum of Neoplastic Diseases, Scand. J. Immunl. Vo. 9, pp. 193–198 (1984).
John H. Weisburger, Causes, Relevant Mechanisms, and Prevention of Large Bowel Cancer, Seminars in Oncology, vol. 18, No. 4, pp. 316–336 (1991).

* cited by examiner

*Primary Examiner*—Mark Navarro
(74) *Attorney, Agent, or Firm*—Fulbright & Jaworski L.L.P.

(57) ABSTRACT

This invention relates to a combination of immunotherapy and chemotherapy to promote tumor regression by treating a patient in need thereof with a combination of a humanized antibody that binds to A33 antigen and one or more chemotherapeutic agents. The method is useful for treating patients with colorectal cancer and gastric carcinomas. The method is particularly useful for treating patients who have tumors that are resistant to one or more chemotherapeutic agents and/or have metastasized.

28 Claims, No Drawings

METHOD FOR TREATING CANCER USING A33 SPECIFIC ANTIBODIES AND CHEMOTHERAPEUTIC AGENTS

FIELD OF THE INVENTION

This invention relates to a combination of immunotherapy and chemotherapy to promote tumor regression, particularly colorectal cancer and gastric carcinomas by treating a patient in need thereof with a combination of a humanized antibody that binds to A33 antigen and one or more chemotherapeutic agents. The combination of immunotherapy and chemotherapy is also useful for treatment of tumors that are resistant to one or more chemotherapeutic agents.

BACKGROUND OF THE INVENTION

Colorectal cancer remains a major medical problem in the western world, with an estimated 130,000 new cases and 55,000 deaths in the United States in 1997 (Parker S. L., et al., *Cancer statistics* (1997). CA Cancer J Clin., 47:5–27 (1997)). In recent years, dietary and genetic factors have been identified as playing a role in determining an individual's risk of developing the disease (Weisburger, "Causes, relevant mechanisms, and prevention of large bowel cancer", *Seminars in Oncology*, 18:316–336 (1991) and Lynch et al. "Hereditary colorectal cancer", *Seminars in Onocology;* 18:337–366 (1991).

Adjuvant chemotherapy, radiation therapy, and immunotherapy have shown some usefulness in the treatment of primary and advanced colorectal carcinoma but additional agents and regimens are needed to consistently treat these diseases successfully (Petrelli et al., "The modulation of flourouracil with leucovorin in metastatic colorectal carcinoma: A prospective randomized phase III trial", *J Clin Oncol*, 7:1419–1426 (1989); Laurie et al., "Surgical adjuvant therapy of large-bowel carcinoma: An evaluation of levamisole and the combination of levamisole and flourouracil", *J Cin. Oncol.;* 7:1447–1456 (1989); Byfield, et al., "Pharmacological requirements for obtaining sensitization of human cancer cells in vitro to combined 5-FU or ftorafur and X-rays", *Int J Rad Oncol Biol Phys*, 8:1923–1933 (1982); Mohiuddin and Marks, "Adjuvant radiation therapy for colon and rectal cancer", *Sem. Oncol.*18:411–420 (1991); Krook, et al., "Effective surgical adjuvant therapy for high-risk rectal carcinoma", *N Engl. J. Med.*, 324:709–815 (1991) U.S. Pat. No. 5,851,526 and U.S. Pat. No. 5,958,412).

Chemotherapy alone has limitations in that the cancer cells often become resistant to a broad spectrum of structurally unrelated chemotherapeutic agents. Such resistance, termed "multidrug resistance" (MDR), is not an uncommon problem in the treatment of patients with cancer and while significant efforts have been made to understand the mechanisms responsible for MDR, that understanding has not fulfilled the expectations for eradicating chemoresistant cancer cells.

Immunotherapy, alone or in combination with radiotherapy, has also been investigated as a method for inhibiting or eradicating cancer cells. In such treatments the immunoglobulin molecules are preferably specific for an antigen expressed on the cancer cells. In the case of colorectal cancers, radiolabelled antibodies specific for A33 antigen have shown promise for targeting colon cancer cells. The original mouse mAb A33 is an $IgG_2$ a antibody that detects an epitope that is specific to colorectal cancer cells. Biopsy-based radioimmunolocalization studies quantitatively demonstrated high levels of antibody targeting to colorectal cancer.

A33 is a novel glycoprotein with a molecular weight of 43 kD in its monomeric form in Western blots under non-reducing conditions. Extensive immunohistochemical analysis of malignant and normal tissues has demonstrated that the antigen is homogeneously expressed by more than 95% of colon cancers and in the normal colon mucosa but not in other epithelial tissues. Immunohistochemical staining of the normal colon mucosa with serially diluted samples of mAb A33 suggests that A33 antigen expression is greatest at the top of the crypt and minimal at the base. A subset of gastric carcinomas also express the A33 antigen, while normal gastric mucosa are antigen-negative. The A33 antigen has been purified from human colon cancer cells, the protein sequence determined, the cDNA cloned, and the mouse homolog identified. See, U.S. Pat. No. 5,712,369.

The biodistribution and imaging characteristics of $^{131}$I-mAb A33 were studied in colon carcinoma patients with hepatic metastases. Control mAb TA99 studies showed that mAb A33 localization was antigen-specific, cancer:liver ratios were 2.3- to 45-fold higher for specific antibody as compared to non-specific antibodies. In metastatic lesions, the radioisotope is localized primarily in the viable periphery, but even the necrotic core concentrates mAb A33. External imaging shows isotope visualization in the bowel of some patients (Welt S. et al., "Quantitative analysis of antibody localization in human metastatic colon cancer", A phase I study of monoclonal antibody A33, *J Clin. Oncol.;* 8:1894–1906(1990)).

mAb A33 localization is specific with regard to cancer blood pool (as determined by ratios of cancer:liver of injected $^{99}$Tc-HSA) and with regard to an isotype-matched control antibody. Autoradiographs of cancers and surrounding tissue of patients treated with radiolabeled antibody demonstrate that isotope accumulation in cancers corresponds to antibody binding specifically to the cancer cells while the surrounding stromal cells and vasculature do not concentrate the isotope.

A phase II study of $^{131}$I-A33 radioimmunotherapy (Welt S. et al., "Phase I/II study of $^{131}$I-labeled monoclonal antibody A33 in patients with advanced colon cancer", *J Clin Oncol*, 12:1561–1571 (1994)) demonstrated $^{131}$I mAb-A33 had modest anticancer effects in heavily pre-treated patients who were no longer responding to chemotherapy. Of 23 patients treated, five had mixed responses: one patient displayed a disappearance of ascites and a drop in carcinoembryogenic antigen (CEA) levels from 4,200 ng/ml to 1,740 ng/ml, while other radiographic evidence of disease remained stable; in another patient with several pulmonary nodules, a single nodule disappeared while other evidence of disease remained stable; an additional patient with a nonmeasurable, pleura-based mass had a 30% decrease in CEA; and in another patient with progressive abdominal disease, several large lymph nodes of the neck disappeared. The fifth patient also showed a drop in CEA. These results show that murine $^{131}$I-mAb A33 has modest anti-cancer activity in heavily pretreated patients even after a single dose.

Five patients were treated with a second course of $^{131}$I-mAb A33 at 6–16 weeks; however, clearance of radiolabeled mAb was rapid, due to the human antimouse response (HAMA), and localization of isotope to the cancer sites was much less than after the first treatment, indicating that re-treatment is not practical.

An attractive feature of the A33 antigenic system for radioimmunotherapy is the in vitro evidence for rapid internalization of A33 antigen/antibody complexes into colon cancer cells (Daghighian et al., "Enhancement of radiation dose to the nucleus by vesicular internalization of $^{125}$I-labeled A33 monoclonal antibody", *J. Nucl. Med.;* 37:1052–1057 (1996)) and the ability of $^{125}$I-mAb A33-conjugates internalized into the cell to kill colon cancer cells in vitro and in a nu—nu mouse xenograft model. $^{125}$I-mAb A33 exerts its cytotoxic effects primarily through short-range Auger electrons, which are most effective if generated in close proximity (<1–4 μm) to the cell nucleus. Compared to "$^3$I-mAb A33, one of the expected benefits of $^{125}$I-mAb A33 is reduced bone marrow toxicity, and this expectation has been confirmed in the nu—nu mouse cancer model.

In a phase I/II study, twenty-one patients with advanced measurable or evaluable colon cancer who had failed at least one 5-fluorouracil (5-FU) based therapy but had not received prior radiotherapy, were treated with a single dose of $^{125}$I-labeled mAb A33 (Welt et al., "Phase I/II study of Iodine 125-labeled monoclonal antibody A33 in patients with advanced colon cancer", *J. Clin. Oncol.,* 14:1787–1797 (1996)). Of the 20 patients showing radiologic evidence of disease all displayed localization of $^{125}$I to sites of disease. Minor anti-cancer activity was also observed; levels of CEA returned to normal in one patient and decreased by 35% and 23% in two patients, respectively and one additional patient had a mixed response on CT. CEA is a marker associated with cancers, e.g., colon carcinoma and other metastatic cancers (Weinstein et al., "Acute-phase proteins or tumour markers: The role of SAA, SAP, CRP and CEA as indicators of metastasis in a broad spectrum of neoplastic diseases", *Scand J Immunol;* 19:193–8 (1984)). The use of the murine antibody specific for A33 was limited, due to the development of human antimouse antibody production (HAMA). Patients were on the study for only 6 weeks and were then given the option of chemotherapy.

Combination therapies, e.g., combinations of radiotherapy, chemotherapy and immunotherapy have been investigated in naive mice that had not been exposed to chemotherapy prior to the combination therapy (see e.g., Tschmelitsch et al., "Enhanced Anticancer activity of combination radioimmunotherapy: $^{31}$I-Labeled Mononclonal Antibody A33 With Chemotherapy (Fluorouracil)", *Cancer Res.,* 57:2181–2186 (1997)). Radioimmunotherapy with a radiolabeled mouse monoclonal antibody specific for the A33 antigen has been associated with a decrease in levels of serum CEA in patients who have failed conventional chemotherapy (Welt et al., *J. Clin. Oncol.,* 14(6):1787–1797 (1996)). Some reports have suggested that the combination of chemotherapy and antibody-directed immune effector function enhances cancer cell lysis (Segerling et al., "Chemotherapeutic drugs increase killing of tumor cells by antibody and complement", *Science,* 188(4183):55–57 (1975) and Segerling et al., Enhancing effect by metabolic inhibitors on the killing of tumor cells by antibody and complement", *Cancer Res.,* 35:3195–3203 (1975)). Agents with better anti-cancer activity and more effective treatment regimens are still needed if significant progress is to be made in the future.

Described herein is a method for promoting tumor regression by administering one or more chemotherapeutic agents and an antibody specific for the A33 antigen to patients in need thereof. The methods are useful for treating patients whose tumors are chemoresistant to one or more chemotherapeutic agents. The methods are suitable for treating patients having solid tumors and/or tumors that have metastasized. The methods described herein are suitable for use with patients whose tumors are metastatic and chemoresistant. Patients having chemoresitant cancers responded unexpectedly well to the combination of immunotherapy and chemotherapy as compared to the chemotherapy or immunotherapy alone. The methods promoted cancer regression even where the antibody was a non-radiolabelled antibody. In addition, these positive results in patients with chemoresistant tumors suggest that the treatment regimen described herein would also be appropriate for the treatment of patients whose tumors had not become chemoresistant.

SUMMARY OF THE INVENTION

This invention relates to methods for promoting regression of cancer cells, particularly those expressing A33, with a combination of chemotherapeutic agents and immunotherapy. Previously, multidrug combinations, e.g., MOF-Strep (Methyl CCNU, fluorouracil, vincristine and streptozocin) showed significant responses in two initial trials (32–34% overall major response rated) but, in subsequent larger studies, the response rate was lower, resulting in a loss of interest in this combination as an effective cancer treatment. (Kemeny et al., "Therapy for metastatic colorectal carcinoma with a combination of methyl-CCNU, 5-fluorouracil, vincristine and streptozocin", *Cancer* 45:876–881(1980); Kemeny et al., "Metastatic colorectal carcinoma: A prospective randomized trial of methyl-CCNU, 5-flourouracil (5-FU) and vincristine (MOF) versus MOF plus streptozocin (MOF-Strep)", *Cancer,* 51:20–24 (1983)). Recently, there has been renewed interest in combinations of BCNU (carmustine) and streptozocin due to their synergistic activities (see, e.g., Wilson et al., "Modulation of O6-alkylguanine alkyltransferase-directed DNA repair in metastatic colon cancers", *J. Clin Oncol* 1995; 13:2301–2308 (1995) and Preuss et al., "Protective effect of O6-methylguanine-DNA methyltransferase (MGMT) on the cytotoxic and recombinogenic activity of different antineoplastic drugs." *Int J Cancer,* 65:506–512 (1996)). In addition, immune-mediated mechanisms such as ADCC have been shown to be potentiated with cytotoxic reagents (Pfeifer and Bosmann, "Modulation of anticancer antibody-dependent cellular cytotoxicity and natural killer activity by Adriamycin and daunorubicin", *Agents Action,* 12:635–644 (1982), and Schlager and Ohanian, "Role of membrane lipids in the immunological killing of cancer cells: I. Target cell lipids", *Lipids,* 18:475–482(1983)).

The methods of this invention are particularly efficacious for patients having cancer cells that display resistance to one or more chemotherapeutic agents, e.g., the growth rate of the resistant cancer cells is not retarded, new cancer foci continue to emerge, and/or the cancer foci do not display significant reduction in size in response to chemotherapeutic treatments. The chemoresistant cancers may be resistant to the same chemotherapeutic agent that is used in combination with the A33-specific antibody. Co-assigned U.S. Pat. Nos. 5,851,526 and 5,958,412, incorporated herein by reference, disclose methods for treating colon cancer using cancer-specific antibodies conjugated with a radioisotope or an anti-cancer drug. It is disclosed herein that a higher than expected proportion of patients responded favorably to the regimen of chemotherapeutic agents in combination with A33 specific antibodies. Thus far 3/12 patients responded favorably in sharp contrast to treatments with only chemotherapeutic agents where only 10% of patients with chemoresistant tumors responded to the treatment. The patients described herein responded well even though the antibody was not labeled with a radioisotope or other anticancer label. This is the first demonstration in humans of an enhancement of antitumor effects in solid tumors when immune mediated killing of cancer cells directed by antibodies is combined with chemotherapy.

Described herein is the a method for promoting regression of cancer cells expressing A33 antigen by treating a patient having such cancer cells with a combination of immunotherapy and chemotherapy, preferably an antibody specific for A33 antigen and one or more chemotherapeutic agents. The A33-specific antibody(s) and one or more chemotherapeutic agents are administered in sufficient amounts to promote regression of the cancer. Sufficient amounts slow the growth rate of cancer cells, reduce the appearance of new cancer foci, reduce the size of tumors and/or reduce the levels of serum CEA. The chemotherapeutic agents may be administered prior to, concurrently with, or after A33 specific antibody is administered to the patient. Preferably the A33 specific antibody and chemotherapeutic agents are administered concurrently. More preferably the A33 specific antibody is used in combination with one or more chemotherapeutic agents selected from the group consisting of oxaliplatin, irinotecan, topotecan, carmustine, vincristine, fluorouracil, leucovorin and streptozocin. Even more preferably the chemotherapeutic agent is selected from the group consisting of carmustine, vincristine, fluorouracil, leucovorin and streptozocin. Most preferably the A33 specific antibody is administered in conjunction with BOF-Strep (carmustine, vincristine, fluorouracil, and steptozocin).

The A33 specific antibody may be chimeric, multimeric, hetreomeric or single chain form of the antibody. For example the antibody may be a diabody, a triabody or a tetrabody. Preferably the A33 specific antibody is a humanized antibody.

DETAILED DESCRIPTION OF THE INVENTION

The methods described herein comprise administering to a patient in need thereof a combination of chemotherapeutic agents and immunoglobulins specific of an antigen expressed on cancer cells. Preferably the antigen is an A33 antigen and preferably the immunoglobulin molecule is a humanized immunoglobulin molecule. More preferably a humanized antibody is one with a strong effector cell-mediated cytotoxicity. Strong effector cell mediated cytotoxicity is measured using routine methods well known in the art such as e.g, a chromium release assay. Preferably the chemotherapeutic agents and immunoglobulins are administered to the patient concurrently. The combination of chemotherapy, particularly BOF-strep (carmustine, fluorouracil, vincristine and streptozocin) and immunotherapy applied to subjects having chemoresistant cancer cells, i.e., cancer cells that had become resistant to one or more chemotherapeutic agents, promote unexpectedly higher cancer cell regression than chemotherapy or immunotherapy alone. Patients with chemoresistant cancer cells were not expected to respond to the combination of immunotherapy and chemotherapy any better than patients with chemoresitant cancers who were treated with only immunotherapy or chemotherapy.

Those of skill in the art who routinely treat patients with colorectal cancer are aware that there are many different regimens for the treatment of such cancers and the application of those regimens to particular patients will depend on the consideration of a variety of factors, e.g., the stage of the cancer, the extent of the spread of the cancer cells, e.g. have they metastasized, and the physical attributes of the patient. Those of skill in the art routinely adjust the parameters of a particular treatment, e.g., dose, duration, administration route and administered form, for particular patients and those parameters are adjusted without undue experimentation by one of ordinary skill in the art. Many chemotherapeutic protocols, the criteria for their modification and the factors which contraindicate their application are set forth in, e.g., Table 1, and reviews in *Seminars in Oncology*, 26(5) and 26(6) (1999).

TABLE 1

| Toxicity (NCI Grades 1–4)[1] | Strep[2] Week 1 Week 6 | Strep[2] Week 2–5 Week 7–10 | 5-FU*[2] | BCNU*[2] | Vincristine |
|---|---|---|---|---|---|
| Leukopenia | | | | | |
| 1 (<4.0–3.0 × $10^9$/L) | 100% | 100% | 100% | 100% | 100% |
| 2 (2.0–<3.0 × $10^9$/L) | 100% | Hold[3] | 100% | 100% | 100% |
| 3 (1.0–<2.0 × $10^9$/L) | 100% | Hold | If nadir in wk 2, 3 & 7, 8: 80% | If nadir in wk 4, 5: 60% | 100% |
| 4 (<1.0 × $10^9$/L) | 100% | Hold | If nadir in wk 2, 3 & 7,8: 60% | If nadir in wk 4, 5: 60% | 100% |
| Thrombocytopenia | | | | | |
| 1 (<160–75.0 × $10^9$/L) | 100% | If <100 × $10^9$/L Hold | 100% | 100% | 100% |
| 2 (50.0–<75.0 × $10^9$/L) | 100% | Hold | 100% | 100% | 100% |
| 3.(10.0–<50.0 × $10^9$/L) | 100% | Hold | If nadir in wk 2, 3 & 7,8: 80% | If nadir in wk 4, 5: 80% | 100% |

TABLE 1-continued

| Toxicity (NCI Grades 1–4)[1] | Strep[2] Week 1 Week 6 | Strep[2] Week 2–5 Week 7–10 | 5-FU*[2] | BCNU*[2] | Vincristine |
|---|---|---|---|---|---|
| 4 (<10.0 × 10⁹/L) | 100% | Hold | If nadir in wk 2, 3 & 7, 8: 60% | If nadir in wk 4, 5: 60% | 100% |
| Total Bilirubin | | | | | |
| 1 (>1.0–2.5 × ULN) | 100% | 100% | 100% | 100% | >1.0–1.5 × ULN: 50% >1.5–2.5 × ULN: Hold |
| 2 (>2.5–5.0 × ULN) | 100% | 100% | Hold | Hold | Hold |
| 3 (>5.0–20.0 × ULN) | 100% | 100% | Hold | Hold | Hold |
| 4 (>20.2 × ULN) | 100% | 100% | Hold | Hold | Hold |
| Diarrhea | | | | | |
| 1 | 100% | 100% | 100% | 100% | 100% |
| 2 | 100% | 100% | 100% | 100% | 100% |
| 3 | 100% | Hold[3] | 80% | 100% | 100% |
| 4 | 100% | Hold | 60% | 100% | 100% |
| Other Non-hematologic Toxicities | | | | | |
| 1 | 100% | 100% | 100% | 100% | 100% |
| 2 | 100% | 100% | 100% | 100% | 100% |
| 3 | 100% | Hold | 80% | 100% | 100% |
| 4 | 100% | Hold | 60% | 100% | 100% |

[1]Toxicity National Cancer Institute (NCI) Grades 1–4 are followed by the characteristic number of cells per liter for leukopenia and thrombocytopenia. Total bilirubin associated with the particular NCI grades is recited as multiple of the upper limit of normal (ULN), upper limit set at "1". The toxicity parameters were assayed once a week and depending on the NCI grade the dose of chemotherapeutic agent was adjusted such that the patient received a percentage of a predetermined dose.
[2]Strep = Streptozocin; 5-FU* = 5-fluorouracil, and; BCNU* = carmustine.
[3]Hold The chemotherapeutic agent was not administered for the week the measurement was taken.

The results presented herein demonstrate that the addition of A33 specific antibodies to a chemotherapeutic regimen effectively promotes regression of cancer cells that had developed resistance to chemotherapeutic agents. The regression is manifested by slowing the growth rate, reducing the incidence of new cancer foci emerging, and/or reducing the size of the cancer foci. Regression of the cancer can also be measured by assaying the CEA levels within the treated patients. A reduction in CEA levels is indicative of a regression of the cancer mass. CEA levels may be measured using any method known in the art.

The methods described herein combine administering an antibody specific for the A33 antigen and at least one, and preferably a combination, of chemotherapeutic agents. Preferably the chemotherapeutic agents are oxaliplatin, irinotecan, topotecan, leucovorin, carmustine, vincristine, fluorouracil and/or streptozocin. These chemotherapeutic agents are commercially available to those of skill in the art. More preferably the A33-specific antibody is combined with one or more chemotherapeutic agents selected from the group consisting of carmustine, vincristine, fluorouracil or streptozocin. Most preferably the A33 specific antibody is administered in combination with BOF-Strep (carmustine, vincristine, fluorouracil or streptozocin).

Preferably the A33 specific antibody is a monoclonal antibody. Monoclonal antibodies are obtainable via many methods well known in the art. For example, the Kohler-Millstein method, is one such well-known method comprising immunizing an experimental animal, preferably a mouse, with the appropriate protein, isolating antibody-producing B cells or spleen cells from the immunized experimental animal and subsequently fusing the antibody-producing cells with a suitable leukemia cell to produce hybridomas (Kohler and Millstein, "Derivation of specific antibody-producing tissue culture and cancer lines by cell fusion" Eur. J Immunol. 6:511–519 (1976); Kohler-Millstein et al., Methods Enz. 73:1 (1981)). Monoclonal antibodies may also be generated and isolated from phage display libraries. The construction and screening of phage display libraries are well known in the art, see, e.g., Hoogenboom, "Designing and optimizing library selection strategies for generating high affinity antibodies" Trends Biotechnol., 15:62–70 (1997); Hoogenboom, et al. "Antibody phage display technology and its applications", Immunotechnology 4:1–20 (1998); McGregor, "Selection of proteins and peptides from libraries displayed o filamentous bacteriophage", Mol. Biotechnol, 6:155–62 (1996); Bird et al., "Single-chain antigen binding proteins", Science, 242:423–426 (1988); Perisic et al., Structure 2:1217–1226 (1994); Pei et al., PNAS, 94:9637–9642 (1997); Hollinger et al., Protein Engineering 9:299–305 (1996); Millstein and Cuello, Nature 305, 537–539 (1983); Yamanaka et al. (1996). "Chicken monoclonal antibody isolated by a phage display system." J Immunol., 175(3): 1156–1162 (1996) all incorporated herein by reference.) More preferably the monoclonal antibody is a humanized monoclonal antibody.

Humanized antibodies may be chimeric immunoglobulins, immunoglobulin chains or fragments thereof (such as Fv, Fab, Fab', F(ab')$_2$ or other antigen-binding sub-sequences of antibodies) containing a minimal amount of sequence derived from non-human immunoglobulins. For the most part, humanized antibodies are human immunoglobulins in which complementarity-determining regions (CDR) are replaced by CDRs of a non-human species (donor antibody) such as mouse, rat or rabbit having the desired specificity and/or affinity. Methods for the production of humanized antibodies are also known in the art. See e.g., Cabilly, et al., U.S. Pat. No. 4,816,567; Mage & Lamoyi, in Monoclonal Antibody Production Techniques and Applications, pp. 79–97 (Marcel Dekker, Inc., New York, 1987); Jones et al., *Nature,* 321:522–525 (1986); Reichmann et al., *Nature,* 332:323–329 (1988); and Presta, *Curr. Op. Struct. Biol.,* 2:593–596 (1992). Preferably the humanized A33 antibody is a fully humanized CDR-grafted A33 IgG1 antibody (huA33).

The A33-specific antibody may be a chimeric, multivalent, multimeric, or heteromeric form of the antibody. For example, the antibody may be a diabody, a single chain Fv, a triabody or a tetrabody. Those of skill in the art are familiar with methods for the production of such antibody forms, see e.g., Perisic et al., *Structure* 2:1217–1226 (1994); Pei et al., *PNAS,* 94:9637–9642 (1997); Hollinger et al., *Protein Engineering* 9:299–305 (1996); Millstein and Cuello, *Nature* 305, 537–539 (1983) incorporated herein by reference.

An A33 specific antibody may be administered with chemotherapeutic agents and with another antibody conjugate. The additional antibody may be conjugated with a radioisotope or another chemotherapeutic or cytotoxic agent. The radioisotope may be for example, $^{125}$I, $^{131}$I, $^{99}$Tc, $^{90}$Y and $^{111}$In. The A33-specific antibody may also be conjugated to a radioisotope e.g., $^{125}$I, $^{131}$I, $^{99}$Tc, $^{90}$Y, $^{111}$In and other α, β and Auger emitters, or a chemotherapeutic or cytotoxic agent. Those of skill in the art will appreciate that there are many suitable methods for the conjugation of an antibody with a radioisotope, e.g., U.S. Pat. Nos. 5,160,723 and 5,851,526, incorporated herein by reference. The antibody may be conjugated with a chemotherapeutic agent, such as those recited supra, or a cytotoxic agent. For example, huA33 can be conjugated with QFA, which is an antifolate, or with calicheamicin, which is an anti-cancer antibiotic that cleaves double-stranded DNA of cancer cells. Both QFA and calicheamicin have intracellular sites of action and do not readily cross the plasma membrane. As such, they have weak cytotoxic effects when added to cell cultures. Cellular uptake of these agents through huA33-mediated internalization greatly enhances their cytotoxic effects in vitro. In vivo xenograft studies show that cancer inhibition with limited normal tissue damage can be obtained with both huA33-QFA and huA33-calicheamicin conjugates. Other conjugation partners can also be conjugated to the antibodies of the invention e.g., enzymes, prodrugs, and cytotoxic agents e.g., BCNU, mercaptopurine, methotrexate or adriamycin. Any method known in the art for preparing antibody conjugates may be used to generate the conjugates of this invention.

The chemotherapeutic agents may be administered prior to, concurrently with, or after the A33 specific antibody has been administered to the patient. Preferably the A33 specific antibody is administered to a patient repeatedly, preferably in one week intervals. More preferably the A33 specific antibody is administered to the patient once a week for at least about 10 weeks, preferably at least about 14 weeks. Each administration of the A33 specific antibody is preferably a pharmaceutically effective amount, so as to reduce the effects of colon cancer, preferably about 2 to about 100 mg/m$^2$. Preferably the patient in need thereof is pretreated with a regimen of A33-specific antibody without a chemotherapeutic agent before the chemotherapeutic agents are added to the regimen for concurrent treatment with both the antibody and the chemotherapeutic agent(s). Preferably A33 specific antibody is administered to the patient for several weeks, preferably about 4 to 6 weeks, more preferably about 5 weeks, before the chemotherapeutic agents are added to the regimen.

The chemotherapeutic agents, oxaliplatin, irinotecan, topotecan, leucovorin, carmustine, vincristine, fluorouracil and/or streptozocin, may be administered to the patient sequentially or concurrently or in combinations that are used routinely in the art. For example, in one embodiment, carmustine, vincristine, fluorouracil or streptozotocin (BOF-Strep) are administered to the patient in a regimen that is similar to that described by Kemeny et al., "Metastatic colorectal carcinoma: A prospective randomized trial of methyl-CCNU, 5-fluorouracil (5-FU) and vincristine (MOD) versus MOF plus streptozocin (MOF-Strep)", *Cancer,* 51:20–24 (1983) incorporated herein by reference). BOF-Strep may be administered to the patient then, preferably, about one day later and then once a day for several days, preferably about 4 days, carmustine and fluorouracil but not vincristine or streptozocin are administered to the patient. Thereafter streptozocin, but not carmustine, fluorouracil or vincristine, is administered to the patient once a week for about 4–6 weeks, preferably about 4 weeks. This administration of streptozocin is followed by administration of fluorouracil, vincristine, and streptozocin, preferably a single dose of these three agents is administered to the patient. After the administration of the fluorouracil, vincristine, and streptozocin, fluorouracil, but not carmustine, vincristine or streptozocin are administered to the patient once a day for about 3 to 6 consecutive days, preferably about 4 days. Thereafter, streptozocin, but not carmustine, fluorouracil or vincristine is administered to the patient once a week for about 3 to 6 weeks, preferably about 4 weeks. During the administration of the chemotherapeutic agents the patient is also receiving the A33 specific antibody about once a week. This regimen of chemotherapeutic agents and A33 specific antibody may be repeated as often as desired. Preferably carmustine is administered at a dose of about 20 mg/m$^2$ to about 40 mg/m$^2$, more preferably about 30 mg/m$^2$. Preferably vincristine is administered at a dose of about 0.5 mg/m$^2$ to about 2 mg/m$^2$, more preferably about 1.0 mg/m$^2$. Preferably fluorouracil is administered at a dose of about 200 mg/m$^2$ to about 400 mg/m$^2$, more preferably about 300 mg/m$^2$. Preferably, streptozocin is administered at a dose of about 250 mg/m$^2$ to about 750 mg/m$^2$, more preferably about 500 mg/m$^2$. Those of skill in the art can easily determine suitable dosages of each chemotherapeutic agents depending on the characteristics of the individual patient, e.g., the size of the patient and on the response of the patient to the agents. For example, Table 1 demonstrates art-accepted suggestions for the quantity of the agents.

The A33 specific antibody may be a humanized antibody. Methods for humanizing antibodies are well known in the art, see e.g., Daugherty et al., *Nucl. Acids Res.,* 19:2471–2476 (1991), King et al, *Cancer Res.,* 54:6176–6185 (1994), and U.S. Pat. No. 5,821,526, incorporated herein by reference. Preferably the humanized antibody is a fully humanized monoclonal antibody. In one embodiment of this invention a fully humanized CDR-grafted A33 IgG1 (huA33) was used. This humanized IgG1 version of mouse A33 antibody activates immune effector function and in phase I–II trials, huA33 alone was found to have modest anti-cancer activity. HuA33 is equivalent to murine mAb A33 in competitive binding assays and in localization studies in a nu—nu mouse model (Tschmelitsch et al., *Cancer Res.*, 57:2181–2186 (1997)). Radio-iodinated huA33 retains immunoreactivity and repeated administration of huA33 to cynomolgus monkeys for up to one year demonstrates that the antibody is not immunogenic in primates; however, unlike the original mouse IgG2a antibody, huA33 has strong effector cell-mediated cytotoxicity, especially against A33-expressing cancer cell lines which retain >400,000 antibody molecules on their cell surface after the bulk of the bound huA33 is internalized.

EXAMPLES

Preparation of Antibody
Humanized Antibody Specific for A33 (HuA33)

Supernatant containing huA33 (Lot 1) was collected from A33 hybridoma cells grown in bioreactors. Cell-free, sterile-filtered, concentrated supernatant was shipped frozen and stored at −78° C. until it was purified.

Supernatant containing huA33(Lot 2) was collected from A33 hybridoma cells grown in bioreactors. The supernatant was stored at −20° C. to await the purification process.
Purification of HuA33

Purification of huA33 (Lot 1) was performed under sterile conditions by a three-step column chromatography process: Q-Sepharose ion-exchange, proteinA affinity and S-Sepharose ion-exchange chromatography. Column gel bed volumes measured 4.8 cm×48 cm, and a flow rate of 110 cm/hr was used throughout. All procedures except the virus inactivation step were performed at 4° C. Prior to each column run, the tubing and UV detection cell were washed with a chlorine solution and 0.2 M glycine, 150 mM NaCl buffer, pH 2.8, and 50 mM Tris, 150 mM NaCl, pH 8.0, containing 0.1% sodium azide (storage buffer).

For each purification run, two liters of supernatant were thawed, sterile-filtered, adjusted to pH 8.0 with Tris buffer, pH 8.5, and loaded on a Q-Sepharose fast-flow column equilibrated with 50 mM Tris, 0.15 M NaCl buffer, pH 8.0. Antibody does not bind to this column, but DNA and other cell culture contaminants are removed. The Ig fraction was eluted with the same buffer, sterile-filtered, and loaded on a proteinA-Sepharose fastflow column equilibrated with 50 mM Tris, 0.15 M NaCl buffer, pH 8.0. The column was washed with eight column volumes of equilibrated buffer followed by three column volumes of 50 mM citric acid, 0.15 M NaCl buffer, pH 6.0. The Ig fraction was eluted with 50 mM citric acid, 0.15 M NaCl buffer, pH 3.0. A virus inactivation procedure was performed by adjusting the Ig pool to pH 3.0 with 1.0 M citric acid, pH 3.0, at this stage and incubating at room temperature for 30 min. The Ig pool was diluted ⅕ with cold 5 mM sodium acetate buffer, pH 5.9, and loaded on an S-Sepharose fast-flow column equilibrated with the same buffer. Ig binds to this column. Following a wash of 1.5 column volumes of equilibration buffer and three column volumes of 50 mM sodium phosphate, pH 6.0, the purified Ig was eluted with 50 mM phosphoric acid, 0.15 M NaCl, pH 7.0 (PBS), sterile-filtered, and stored at −78° C.

Purification of huA33 (Lot 2) was performed under sterile conditions using a four-step column chromatography process: anion exchange on Q-Sepharose, affinity binding on proteinA Sepharose, cation exchange on SP-Sepharose and size exclusion chromatography on Superdex 200. Column gel bed heights were 29 cm, 14 cm, 13 cm and 54 cm respectively. Flow rates were 100 ml/min for anion exchange and 50 ml/min for affinity and cation exchange chromatography. All procedures except the virus inactivation step were performed at 4° C.: All columns were sanitized with 2 column volumes (CV) of 0.5 N NaOH and stored in 0.1 N NaOH. All buffers were sterile filtered using 0.2 μm filters. The pooled, sterile filtered supernatant, adjusted to pH 8.0 with pH 8.0 Tris/HCl buffer, was loaded onto the Q-Sepharose column which was pre-equilibrated with 2 column volumes of 50 mM Tris/HCl buffer. The antibody passed through whilst contaminating proteins were bound. Elution of the bound fractions was accomplished with 50 mM Tris/1.0 M NaCl. The unbound pool, containing the antibody was sterile filtered using the 0.2 μm filter and loaded onto the Protein A Sepharose column which was pre-equilibrated with 50 mM Tris/HCl buffer, pH 8.0, followed by washing with Tris/HCl buffer, pH 8.0, followed by 50 mM citric acid pH 6.0 to remove the contaminant proteins. The column was then eluted with 50 mM citric acid, pH 3.0 to collect the antibody, followed by immediate virus inactivation step by adjusting the pool to pH 3.5–3.0 using 0.1N HCl and holding for 30 minutes at room temperature. The Protein A column was regenerated with 100 mM glycerine/150 mM NaCl, pH 2.5. Eluates were then diluted 1:3 with 50 mM Tris/HCl buffer, pH 8.0 and pH adjusted to 5.9 using 0.1N NaOH and filtered using 0.2μm filter. The pool was applied to the SP-Sepharose cation exchange column equilibrated with the same buffer, followed by elution with 50 mM Tris/HCl/0.5 NaCl (0–50%). The pool was collected and again sterile filtered. Lastly, the pool was loaded onto the Superdex 200 column which was equilibrated with phosphate buffered saline pH 7.0 (PBS) and then eluted with PBS. The pool was again sterile filtered, antibody determination by absorbance at 280 nm, Size Exclusion Chromatography (size distribution) and BIAcore biosensor assay (binding affinity of the antibody for its antigen).

Stored antibody (−80° C.) was evaluated in ongoing stability trials at intervals over several months for purity/homogeneity (SEC-HPLC), MW determination and homogeneity (SDS-PAGE), enzymatic digestion and mapping, pH determination, endotoxin level, sterility, protein determination by absorbance at 280 nm and biological activity, including affinity and activity assays.
Phase I Study of HuA33

This trial of the humanized version of mAb A33 examined 3 dose levels (10 mg/M$^2$, 25 mg/m$^2$ and 50 mg/m$^2$ per week) given in cycles of 4 weekly doses. As huA33 reacts with normal colon cells, great attention was paid to bowel toxicity; however, no significant bowel toxicity was documented except in two patients treated at the highest dose level, who developed transient grade 1–2 nausea and vomiting immediately after the infusion. All patients were monitored continuously for blood in stool, and only one patient at the 25 mg/m$^2$ dose level developed transient, positive guaiacs. Colonoscopy could not detect a bleeding site, and a random biopsy of the patient's colon mucosa showed no specific abnormalities. Subsequently, the patient's stools became guaiac-negative and remained so for 6 months while treatment with huA33 continued.

Anticancer activity was observed at all three dose levels. After 30 months of treatment, one patient treated at the 10 mg/M$^2$ dose level had a reduction of serum CEA levels from 80 to 3.0 over a 7-month period and achieved a partial response of lung, liver and lymph node metastases by CT analysis. Two patients treated at 25 mg/m$^2$ had serum CEA reductions of 25% and 20%, respectively, with stable CT scans; one of the patients was stable for one year. One patient treated at 50 mg/M² had a 40% reduction in serum CEA levels, followed by metabolic disorders consistent with a cancer lysis syndrome (i.e., uric acid 22.2 mg/dL and LDH 3,200 U/L). Uric acid levels did not significantly decrease with rigorous hydration, and the patient died with progressive renal insufficiency.

Phase II Study of HuA33

This trial examined the response rate of patients with advanced colon cancer to weekly low-dose antibody infusion over 12 weeks. No significant toxicities were observed except for mild eosinophilia. As 10 mg/m² had been determined to be the dose for future radioimmunotherapy studies, one goal of this study was to determine if responses could be obtained with unlabeled huA33 at this dose level and schedule. No major responses were observed in 17 evaluable patients. Two patients achieved stable disease of 10 and 5 months' duration, respectively, and the serum CEA level of one of these patients normalized. As additional lots of huA33 are produced, a high-dose phase II study will be carried out to define the response rate to huA33.

Patient Selection

The patients in this study were at least 18 years of age. They had histologically proven colon or rectal cancer as confirmed by pathological examination. In addition, the patients had unresectable disease (stage IV) and failed conventional chemotherapy for advanced disease or refused other treatment. The patients' disease was measurable by conventional imaging methods including radiographs, ultrasound, computer tomography, or other treatment. For these studies, the patients had not received any chemotherapy, radiotherapy or immunotherapy for at least 4 weeks prior to entry into the study.

Any patient who had a prior administration of mouse monoclonal antimouse antibody or antibody fragment, chimeric or humanized antibody, and/or positive human antimouse antibody (HAMA) titer or a prior treatment with BOF-Strep was excluded from this study.

Protocol Summary

Patients with advanced colon cancer (i.e., those described supra) were treated with a standard chemotherapy regimen, BOF-Strep (Kemeny et al., "Metastatic colorectal carcinoma: A prospective randomized trial of methyl-CCNU, 5-fluorouracil (5-FU) and vincristine (MOD) versus MOF plus streptozotocin (MOF-Strep)",: Cancer, 51:20–24 (1983)) plus immunotherapy with a humanized A33 antibody (huA33). The huA33 dose escalation/toxicity study evaluated cohorts of patients who received increasing doses of huA33 given weekly for 14 weeks and BOF-Strep for 10 weeks starting in week 5 of the antibody treatments. Because the A33 antibody binds to normal colon cells, one objective of this study was to determine whether bowel toxicity is dose-limiting with this immunochemotherapy.

It was observed that some patients treated with murine or humanized A33 antibody, who were subsequently treated with BOF-Strep, had dramatic major responses to the chemotherapy.

Treatment Regimen

Patients were treated in the outpatient immunology treatment area and received huA33 once a week for 14 weeks. Three patients each were treated at 5 mg/m², 10 mg/M², 25 mg/M², 40 mg/M², and 60 mg/m² of huA33 to determine the maximum tolerable dose (MTD). Dose escalation began only after the last patient at the lower dose completed the cycle (end of week 14). Starting in week 5 (day 29), patients began the following (BOF-Strep) chemotherapy regimen (Table 2 and Table 3):

TABLE 2

| Chemotherapeutic agent | Dose | Schedule |
|---|---|---|
| Carmustine | 30 mg/m² | Day 29, 30, 31, 32, 33 |
| Fluorouracil | 200 g/m² | Day 29, 30, 31, 32, 33, 64, 65, 66, 67, 68 |
| Vincristine | 1 mg | day 29,64 |
| Streptozotocin | 500 g/m² | day 29, 36, 43, 50, 57, 64, 71, 78, 85, 92 |

TABLE 3

Flow Sheet

| Cycle: | | +------------------------------------------------------------| |
|---|---|---|
| Week: | Pre-study[1] | 1 2 3 4 5 6 7 8 9 10 11 12 13 14 |
| Day: | | 1 8 15 22 29 36 43 50 57 64 71 78 85 92 |
| HuA33: | | X X X X X X X X X X X X X X |
| Carmustine:[2] | | X→ |
| Fluorouracil:[3] | | X→ X→ |
| Vincristine: | | X X |
| Streptozocin: | | X X X X X X X X X X |
| History: | X | X X X X |
| Physical exam: | X | X X X X |
| Weight & height: | X | X X X X |
| Performance status: | X | X |
| CBC: | X | X X X X X X X X X X X X X X |
| PT, PTT: | X | X X X |
| Comprehensive Chemistry:[4] | X | X X X X |
| Uric acid: | X | X X X X X X X |
| Urinalysis: | X | X X X |
| EKG: | X | |
| CEA: | X | X X X X |
| HAHA: | X | X X X X X X |
| huA33 serum levels:[5] | X | X X X X X X X X X X X X X X |
| Pregnancy test: | X | |

TABLE 3-continued

Flow Sheet

| | | | | | | | | | | | | | |
|---|---|---|---|---|---|---|---|---|---|---|---|---|---|
| Stoll guaiac: | X | X | X | X | | X | X | X | X | X | | X | X | X | X |
| Toxicity questionnaire: | X | X | X | X | | X | X | X | X | X | | X | X | X | X |

[1]Pre-study: within 2 weeks before first huA33 does
Evaluation of measurable disease: CXR, CT scan, bone scan, etc.: Pre-study and at 14 weeks
[2]Carmustine: on days 29, 30, 31, 32 and 33
[3]Fluorouracil: on days 29, 30, 31, 32, 33 and again on days 64, 65, 66, 67 and 68
[4]Comprehensive chemistry panel: Na, K, Cl, Ca, total protein, albumin, creatinine, glucose, BUN, alk phos, total bilirubin, ALT, AST and LDH
[5]huA33 serum levels: 0, 30 and 60 min after each huA33 dose The chemotherapy regimen was designed to be given as five consecutive daily doses on Monday through Friday. (Chemotherapy dose modification for toxicity is outlined in Table 1, supra.) Patients continued to receive huA33, if chemotherapy dose was held or modified. At the end of the 14-week cycle, patients were re-evaluated by radiography. If there was no evidence of disease progression and following recovery from toxicity, they were retreated. The re-treatment cycle consisted of weeks 5–14 (days 29–92) of the first cycle. Therefore, the 4-week pre-treatment with huA33 alone was deleted.

Twelve patients with advanced colorectal cancer resistant to at least 2 chemotherapeutic regimens that contained fluorouracil (12/12 patients) and irinotecan (11/12 patients), were entered into three dose levels (5, 10 and 25 mg/m$^2$) of huA33 in combination with BOF-Strep. Three patients requiring radiotherapy were removed early. Of 9 evaluable patients, one had grade 3 neutropenia and one had grade 3 thrombocytopenia related to chemotherapy. No toxicities due to the combination of immuno-chemotherapy were identified. Of these 9 patients, five developed anti-huA33 activity (HAHA+) as determined by Biacore analysis. HAHA measured by Biacore has been shown to correlate with accelerated antibody clearance. In one HAHA+ case, treatment was discontinued early when rash and puritis developed. Of the 8 patients completing one cycle, two had partial responses (CEA levels dropped from 7845.5 ng/ml to 528.2 ng/ml over 7.5 months and 130.4 ng/ml to 20.1 ng/ml over 5.5 months; one patient had a mixed response (CEA 40.0 ng/ml to 24.9 ng/ml in 4.5 months; and one patient had stable disease after 9 months. No responses were seen when patients were HAHA+. The occurrence of HAHA in patients receiving huA33 has prompted us to develop additional huA33 IgG1 for inclusion in treatment protocols.

The early phase I study (Welt et al., "Phase I/II study of Iodine 125-labeled monoclonal antibody A33 in patients with advanced colon cancer", *J. Clin. Oncol.*, 14:1787–1797 (1996)) analyzed the effects of radiolabelled mouse anti-A33 monoclonal antibodies, $^{125}$I-mAb, on cancer progression in a population of patients who were heavily pretreated with chemotherapy. Modest anticancer activity was observed in this heavily pretreated patient population. After this earlier phase I study of $^{125}$I-mAb, significant responses were seen in patients who received BOF-Strep chemotherapy after administration of radiolabelled murine antibody specific for A33, but responses were seen with BOF-Strep but not with other chemotherapeutic agents, including captothecin-11 (unpublished observations). It is of interest that major responses were seen in 4/8 patients who were treated with BOF-Strep (carmustine, fluorouracil, vincristine and streptozotocin) after the $^{125}$I-mAb A33 trial, but not with other chemotherapeutic agents including camptothecin-11 (CPT-11)(irinotecan). Only 1/11 patients responded to treatments with humanized anti-A33 antibody alone. In the experiments disclosed herein, again, responses were seen with BOF-Strep but not with other chemotherapeutic agents, including captothecin-11.

The foregoing study, which is the first to assess the combination of immunotherapy using huA33 and chemotherapy, and demonstrates that the combination of huA33 and chemotherapy provides an effective means for promoting the regression of cancers, even those that display resistance to one or more chemotherapeutic agents.

We claim:

1. A method for promoting tumor regression in a patient comprising administering to a patient in need thereof:
   (a) a humanized antibody which binds to an A33 antigen wherein said antibody is not labeled with a radioisotope or other anticancer label, and
   (b) at least one chemotherapeutic agent, wherein a said chemotherapeutic agent and humanized antibody are administered in sufficient amounts to promote tumor regression.

2. The method of claim 1, wherein said at least one chemotherapeutic agent is selected from the group consisting of oxaliplatin, irinotecan, topotecan, leucovorin, carmustine, vincristine, fluorouracil and streptozocin.

3. The method of claim 1, wherein at least one chemotherapeutic agent is selected from the group consisting of carmustine, fluorouracil, vincristine and streptozocin.

4. The method of claim 1, wherein carmustine, fluorouracil, vincristine and streptozocin are administered concurrently to said patient subsequent to the administration of the humanized antibody which binds to an A33 antigen.

5. The method of claim 1, wherein carmustine, fluorouracil, vincristine and streptozocin are administered concurrently to said patient from about 4 to about 6 weeks after humanized A33 specific antibody is first administered to said patient.

6. The method of claim 1, wherein carmustine is administered at a dose of 20 to 40 mg/m$^2$.

7. The method of claim 6, wherein carmustine is administered at a dose of 3 mg/m$^2$.

8. The method of claim 1, wherein fluorouracil is administered at a dose of about 200 to about 400 mg/m$^2$/day.

9. The method of claim 8, wherein fluorouracil is administered at a dose of about 300 mg/m$^2$.

10. The method of claim 1, wherein vincristine is administered at a dose of about 0.5 to about 2 mg/m$^2$.

11. The method of claim 10, wherein vincristine is administered at a dose of about 1 mg/m$^2$.

12. The method of claim 1, wherein streptozocin is administered at a dose of about 250 to about 750 mg/m$^2$.

13. The method of claim 12, wherein streptozocin is administered at a dose of about 500 mg/m$^2$.

14. The method of claim 1, wherein said humanized antibody which binds to an A33 antigen is a bispecific, trimeric, heteromeric or single chain form of the antibody.

15. The method of claim 1, wherein said humanized antibody which binds to an A33 antigen is administered at one-week intervals.

16. The method of claim 15, wherein said humanized antibody which binds to an A33 antigen is administered for at least 14 weeks.

17. The method of claim 1, wherein said cancer is a colon cancer or gastric carcinoma.

18. The method of claim 1, wherein about 2 mg/M² to 100 mg/m² of said humanized antibody which binds to an A33 antigen are administered to said patient.

19. The method of claim 2, further comprising administering to said patient a second antibody conjugated with a radioisotope or an chemotherapeutic agent.

20. The method of claim 19, wherein said radioisotope is selected from the group consisting of $^{125}$I, $^{131}$I, $^{99}$Tc, $^{90}$Y and $^{111}$In.

21. The method of claim 19, wherein said chemotherapeutic agent is mercaptopurine, methotrexate or adriamycin.

22. The method of claim 2, wherein said tumors are chemoresistant tumors.

23. The method of claim 1, wherein said tumors are solid tumors.

24. The method of claim 1, wherein said tumors are metastasized tumors.

25. The method of claim 6, wherein the carmustine is administered for about 5 days.

26. The method of claim 8, wherein the fluorouracil is administered for about 5 days.

27. The method of claim 10, wherein the vincristine is administered for about 3 to about 6 days.

28. The method of claim 12, wherein streptozocin is administered for about 4 to about 6 weeks.

* * * * *